(12) United States Patent
Burnet et al.

(10) Patent No.: US 9,550,802 B2
(45) Date of Patent: Jan. 24, 2017

(54) ANTI-INFLAMMATORY MACROLIDES

(71) Applicant: Michael W. Burnet, Tübingen (DE)

(72) Inventors: Michael W. Burnet, Tübingen (DE); Christiane Bauerlein, Ofterdingen (DE); Mary Eggers, Ammerbuch (DE); Jan-Hinrich Guse, Tubingen-Buhl (DE)

(*) Notice: Subject to any disclaimer, the term of this patent is extended or adjusted under 35 U.S.C. 154(b) by 0 days.

(21) Appl. No.: 14/498,311

(22) Filed: Sep. 26, 2014

(65) Prior Publication Data

US 2015/0232499 A1    Aug. 20, 2015

Related U.S. Application Data

(63) Continuation of application No. PCT/US2013/034159, filed on Mar. 27, 2013.

(60) Provisional application No. 61/635,291, filed on Apr. 18, 2012, provisional application No. 61/616,415, filed on Mar. 27, 2012.

(51) Int. Cl.
*C07H 17/08* (2006.01)

(52) U.S. Cl.
CPC ..................... *C07H 17/08* (2013.01)

(58) Field of Classification Search
CPC ...................................... C07H 17/08
USPC ........................................... 536/7.1
See application file for complete search history.

(56) References Cited

U.S. PATENT DOCUMENTS 5,250,518 A    10/1993   Kobrehel et al.

FOREIGN PATENT DOCUMENTS

| WO | WO 99/20639 | * | 4/1999 | ............. C07H 17/08 |
| WO | WO 03/070174 A2 | | 8/2003 | |
| WO | WO 2012/051126 A2 | | 4/2012 | |

OTHER PUBLICATIONS

Mencarelli, A. et al, European Journal of Pharmacology, 2011, 665, 29-39.*
Berge, S.M. et al, Journal of Pharmaceutical Sciences, 1977, 66(1), 1-19.*
Partial Supplementary Search Report mailed Oct. 20, 2015 in connection with EP 13768982.4.
Extended European Search Report mailed Feb. 8, 2016 in connection with EP 13768982.4.
International Search Report and Written Opinion mailed Sep. 6, 2013 in connection with PCT/US2013/034159.
International Preliminary Report on Patentability mailed Oct. 9, 2014 in connection with PCT/US2013/034159.
[No Author Listed] Milestones in Drug Therapy: Macrolide Antibiotics. Eds. Schönfeld and Kirst. Springer Basel AG. 2002:87.
Southern et al., Azithromycin for cystic fibrosis. Eur Respir J. Nov. 2004;24(5):834-8. Review.

* cited by examiner

*Primary Examiner* — Ganapathy Krishnan
(74) *Attorney, Agent, or Firm* — Wolf, Greenfield & Sacks, P.C.

(57) ABSTRACT

The invention provides novel compounds and compositions and methods for making and using the compounds and compositions. In particular, the use of organic acid salts promotes solubility. These more soluble forms are suitable for use in various diseases, notably diseases of lung, muscle, metabolism and eyesight.

4 Claims, 3 Drawing Sheets

Compound 1

Compound 2

Compound 3

Compound 4

Compound 5

Compound 6

Compound 7

Compound 8

Figure 1

Compound 9

Compound 10

Compound 11

Compound 12

Compound 13

Compound 14

Compound 15

ANTI-INFLAMMATORY MACROLIDES

RELATED APPLICATIONS

This application is a continuation of PCT Patent Application No. PCT/US2013/034159, filed Mar. 27, 2013, pending, which claims the benefit of and priority to U.S. Provisional Application No. 61/635,291, filed Apr. 18, 2012, and to U.S. Provisional Application No. 61/616,415, filed Mar. 27, 2012. The contents of each of the foregoing applications are incorporated herein by reference in their entireties.

BACKGROUND

Macrocyclic lactones, and in particular, the "macrolides" are naturally derived and semi-synthetic compounds that are anti-bacterial, anti-inflammatory and also potentially able to modify ion transport (Saint-Criq et al. 2011 B). These biological activities have resulted in the use of Azithromycin, for a wide range of inflammatory diseases mediated by neutrophil activation. In particular, azithromycin is used to decrease airway inflammation and mucus hyper-secretion in patients with diffuse panbronchiolitis, chronic sinusitis, and chronic bronchitis. These properties have also led to the long-term use of azithromycin in cystic fibrosis (CF) where it is unclear whether its primary effect is on airway secretion properties, or on anti-bacterial effects on opportunistic pathogens such as *Psuedomonas aeruginosa*.

Given the observed efficacy of macrolides, notably azithromycin, in various lung diseases, we sought to solve two problems associated with their use. The first is to limit selection for antibiotic resistance associated with long-term use of the material. The second was to identify convenient formulations for inhaled or oral use. In particular, formulations or salts that are particularly soluble in biological solutions.

In a recent disclosure (61/391,679), we described the fact that oxidized descladinosyl macrolides were non-antibacterial in vivo while retaining desirable anti-inflammatory activity especially in lung inflammation. In the process of optimizing the use of macrolides in lung inflammation, we observed that organic salts of macrolides are more soluble in NaCl containing solutions and more suitable for promoting Cl-efflux from cells.

Here we describe novel salts of macrolides with improved solubility, novel pro-drugs of macrolides with improved solubility and associated uses for the treatment of inflammatory diseases of lung, liver, muscle and eye.

SUMMARY OF THE INVENTION

In one aspect, the invention provides novel compounds.
In one embodiment, the invention provides a compound represented by the formula:

in which
R1=H, P(=O)(OH)$_2$, S(=O)$_2$(OH), a saccharide or C(=O)—R4, wherein R4=(CH$_2$)$_2$—C(=O)OH, C(=O)CH=CHC(=O)OH, CH=CHC(=O)OH, or an amino acid;
R2=H, C(=O)(CH$_2$)$_2$C(=O)H, or a saccharide moiety
or a pharmaceutically acceptable salt or formaldehyde adduct thereof.

In another embodiment, the invention provides a compound represented by the formula:

in which
R1=H, acetyl or C(=O)(CH$_2$)$_2$C(=O)OH;
R2=H or C(=O)(CH$_2$)$_2$C(=O)OH [C(=O)(CH$_2$)$_2$C(=O)OH only in case that R1 is C(=O)(CH$_2$)$_2$C(=O)OH];
or a pharmaceutically acceptable salt or formaldehyde adduct thereof.

In another embodiment, the invention provides a compound represented by the formula:

wherein
R1=H, P(=O)(OH)$_2$, S(=O)$_2$(OH), a saccharide or C(=O)—R3, wherein
R3=(CH$_2$)$_2$—C(=O)OH or an amino acid;
or a pharmaceutically acceptable salt or formaldehyde adduct thereof.

In another embodiment, the invention provides a salt of a compound of any of the foregoing structures, wherein the salt comprises an organic acid anion In another embodiment, the invention provides a salt of compound 1 containing an organic acid anion In another embodiment, the invention provides a salt of a compound of of any of the foregoing structures, wherein the salt comprises an anion of an acid selected from the group consisting of acetic, formic, propionic, suberic, malic, citric, maleic, fumaric, succinic, azelaic, pyruvic, alpha ketoglutaric, aspartic, glutamic, sulfonic and ascorbic acids.

In another embodiment, the invention provides a salt of a compound of general formula:

R1 can be but is not limited to
H
$P(=O)(OH)_2$
$S(=O)_2(OH)$
saccharide
$C(=O)—R^6$
$CH_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
$NO_2$
$S(=O)_k(C_1-C_{10})$alkyl;
$S(=O)_k(C_1-C_{10})$alkenyl
$S(=O)_k(C_1-C_{10})$alkynyl
$S(=O)_k(C6-C_{10})$aryl
$S(=O)_k(C_2-C_9)$heteroaryl
wherein k is 0, 1 or 2, and alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $—NR^7R^8$, $R^7C(=O)—$, $R^7C(=O)O—$, $R^7OC(=O)O—$, $R^7NHC(=O)—$, $R^7C(=O)NH—$, $R^7R^8NC(=O)—$, $R^7OC(=O)—$, and $-xNO_2$ with x=O;S;N $R^2$ can be, but is not limited to
H
$—NO_2$
$C(=O)—R^6$
O-(aryl-$R^9$)
or the $R^2$ and $R^3$ bearing atoms are connected via $—C(=O)C—$ (carbonate linkage)

$R^3$ can be but is not limited to
H
or the $R^2$ and $R^3$ bearing atoms are connected via $—C(=O)C—$ (carbonate linkage)

$R^4$ can be, but is not limited to
H
$CH_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
$C(=O)—R^6$
$S(=O)_k(C_1-C_{12})$alkyl
$S(=O)_k(C_1-C_{12})$alkenyl
$S(=O)_k(C_1-C_{12})$alkinyl
$S(=O)_k(C_6-C_{10})$aryl
$S(=O)_k(C_2-C_9)$heteroaryl
wherein k is 0, 1, 2, and alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $—NR^7R^7$, $R^7C(=O)—$, $R^7C(=O)O—$, $R^7OC(=O)O—$, $R^7NHC(=O)—$, $R^7C(=O)NH—$, $R^7R^8NC(=O)—$, $R^7OC(=O)—$, and $-xNO_2$ with x=O;S;N $R^5$ can be, but is not limited to
H
$CH_3$
$C(=O)—R^6$

$R^6$ can be, but is not limited to
Amino acid
$CH_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
$(CH_2)_kCOO(CH_2)_kH$
$(CH_2)_kO(CH_2)_kCOO(CH_2)_kH$
$CH=CHC(=O)OH$
wherein k is 1-10 and k' 0, 1 or 2.

$R^7$, $R^8$ can be independently, but are not limited to
H
$(C_1-C_{10})$alkyl
$(C_1-C_{10})$alkenyl
$(C_1-C_{10})$akynyl
$(C_1-C_8)[C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
wherein alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, and $-xNO_2$ with x=O;S;N
or $N(R^7R^8)$ is an aziridine, azetidine, pyrrolidine, piperidine, azepane or azocane, 1-substituted piperazine, or morpholine moiety $R^9$ can be, but is not limited to:
Halogen
$(C_1-C_3)$alkyl
$NO_2$
CN
$OCH_3$ containing acetic, formic, propionic, suberic, malic, citric, maleic, fumaric, succinic, azelaic, pyruvic, alpha ketoglutaric, aspartic, glutamic, sulfonic and ascorbic acids.

In another embodiment, the invention provides a salt of a compound of general formula:

$R^1$ can be but is not limited to

H, $P(=O)(OH)_2$, $S(=O)_2(OH)$, saccharide, $C(=O)—R^7$,
CH$_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
NO$_2$
$S(=O)_k(C_1-C_{10})$alkyl
$S(=O)_k(C_1-C_{10})$alkenyl
$S(=O)_k(C_1-C_{10})$alkynyl
$S(=O)_k(C6-C_{10})$aryl
$S(=O)_k(C_2-C_9)$heteroaryl wherein k is 0, 1 or 2, and alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, —NR$^8$R$^9$, R$^8$C(=O)—, R$^8$C(=O)O—, R$^8$OC(=O)O—, R$^8$NHC(=O)—, R$^8$C(=O)NH—, R$^8$R$^9$NC(=O)—, R$^8$OC(=O)—, and -xNO$_2$ with x=O;S;N $R^2$ can be, but is not limited to
H
—NO$_2$
C(=O)—R$^6$
O-(aryl-R$^{10}$)
or the R$^2$ and R$^3$ bearing atoms are connected via —C(=O)C— (carbonate linkage)

$R^3$ can be but is not limited to
H
or the R$^2$ and R$^3$ bearing atoms are connected via —C(=O)C— (carbonate linkage)

$R^4$ can be, but is not limited to
H
CH$_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[(C_1-C_4)$alkoxy]alkenyl
$(C_6-C_{10})$aryl-$(C_1-C_5)$alkyl
$(C_2-C_9)$heteroaryl-$(C_1-C_5)$alkyl
C(=O)—R$^6$
$S(=O)_k(C_1-C_{12})$alkyl
$S(=O)_k(C_1-C_{12})$alkenyl
$S(=O)_k(C_1-C_{12})$alkinyl
$S(=O)_k(C_6-C_{10})$aryl
$S(=O)_k(C_2-C_9)$heteroaryl wherein k is 0, 1, 2, and alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, —NR$^8$R$^9$, R$^8$C(=O)—, R$^8$C(=O)O—, R$^8$OC(=O)O—, R$^8$NHC(=O)—, R$^8$C(=O)NH—, R$^8$R$^9$NC(=O)—, R$^8$OC(=O)—, and -xNO$_2$ with x=O;S;N $R^5$ can be, but is not limited to
H
CH$_3$
C(=O)—R$^7$
R6=R1
$R^7$ can be, but is not limited to
Amino acid
CH$_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
$(CH_2)_kCOO(CH_2)_kH$
$(CH_2)_kO(CH_2)_kCOO(CH_2)_kH$
CH=CHC(=O)OH wherein k is 1-10 and k' 0, 1 or 2.

$R^8$, $R^9$ can be independently, but are not limited to
H
$(C_1-C_{10})$alkyl
$(C_1-C_{10})$alkenyl
$(C_1-C_{10})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl wherein alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, and -xNO$_2$ with x=O;S;N or N(R$^7$R$^8$) is an aziridine, azetidine, pyrrolidine, piperidine, azepane or azocane, 1-substituted piperazine, or morpholine moiety $R^{10}$ can be, but is not limited to:
Halogen
$(C_1-C_3)$alkyl
NO$_2$
CN
OCH$_3$
N(CH$_3$)$_2$
N$_3$
SH
S(C$_1$-C$_4$)alkyl containing acetic, formic, propionic, suberic, malic, citric, maleic, fumaric, succinic, azelaic, pyruvic, alpha ketoglutaric, aspartic, glutamic, sulfonic and ascorbic acids.

In one embodiment, the salt of a compound is a salt of compound 1.

In another embodiment, the invention provides a salt of an azilide macrolide containing suberic, maleic, azelaic, pyruvic, alpha ketoglutaric, or ascorbic acid. In certain embodiments, the azilide macrolide is azithromycin.

In another aspect, the invention provides a method of treating an inflammatory disorder, comprising administering to a subject in need thereof an effective amount of a compound or salt described herein. In certain embodiments, the inflammatory disorder is a disease of the lung, muscles, metabolism or eyes.

In another aspect, the invention provides a method of treating an lung disorder, comprising administering to a subject in need thereof an effective amount of a a compound or salt described herein. In certain embodiments, the lung disorder is asthma, COPD, rhinitis, diffuse panbronchiolitis, chronic sinusitis, chronic bronchitis, lung transplant or cystic fibrosis, or particularly cystic fibrosis. In certain embodiments, the compound is compound 1 or salt thereof. In certain embodiments, the muscle disorder is muscular dystrophy. In certain embodiments, the disease of metabolism is type II diabetes. In certain embodiments, the disease of metabolism is chirosis or diabetes secondary to a CFTR mutation or cystic fibrosis.

DETAILED DESCRIPTION

Increased Solubility Using Organic Acid Salts

Macrolide solubility is known to be improved by the addition of acids, however, it is also known that excess acidity results in removal of the cladinose sugar, and or the desosamine sugar. In addition, we were surprised to observe that inorganic acids do not promote the solution of compound 1 in 0.9% saline solutions to the same extent as in water. In contrast solutions with organic acids are more soluble and require fewer equivalents to produce a solution in a solution of 0.9% NaCl in water. The same observations apply for azithromycin and are reported in example 17.

Solubility can therefore be improved by formation of organic salts of azilides, notably azithromycin, and compound 1, including those of 1, 2, 3, 4, 5, 6, 7 and 8 carbon acids, di-acids or tri-acids, acetic, formic, propionic, suberic, malic, citric, maleic, fumaric, succinic, azelaic, pyruvic, alpha ketoglutaric, aspartic, glutamic, sulfonic and ascorbic acids, most preferably at a ratio of between 1.2 and 0.6 acid equivalents per mole of azilide, most preferably in a ratio between 1.0 and 0.7 acid equivalents.

In a more preferred embodiment the acids are: propionic, suberic, malic, pyruvic, alpha ketoglutaric, aspartic, glutamic, and ascorbic acids, This approach can be applied more widely to many compounds. In one embodiment, the members of the compound family (including compound 1) defined as follows:

$R^1$ can be but is not limited to
H
$P(=O)(OH)_2$
$S(=O)_2(OH)$
saccharide
$C(=O)-R^6$
$CH_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
$NO_2$
$S(=O)_k(C_1-C_{10})$alkyl;
$S(=O)_k(C_1-C_{10})$alkenyl
$S(=O)_k(C_1-C_{10})$alkynyl
$S(=O)_k(C_6-C_{10})$aryl
$S(=O)_k(C_2-C_9)$heteroaryl wherein k is 0, 1 or 2, and alkyl, alkenyl, alkynyl are optionally substituted by one to five substituents selected independently from halogen (as can be F, Cl, Br, I), $(C_1-C_4)$alkyl, $(C_1-C_4)$alkenyl, $(C_1-C_4)$alkynyl, $(C_3-C_7)$cycloalkyl, $(C_1-C_6)$heterocycloalkyl, $(C_6-C_{10})$aryl, $(C_1-C_9)$heteroaryl, $(C_1-C_4)$alkoxy, hydroxy, nitro, cyano, azido, mercapto, $-NR^7R^8$, $R^7C(=O)-$, $R^7C(=O)O-$, $R^7OC(=O)O-$, $R^7NHC(=O)-$, $R^7C(=O)NH-$, $R^7R^8NC(=O)-$, $R^7OC(=O)-$, and $-xNO_2$ with x=O;S;N $R^2$ can be, but is not limited to
H
$-NO_2$
$C(=O)-R^6$
$O$-(aryl-$R^9$)
or the $R^2$ and $R^3$ bearing atoms are connected via $-C(=O)C-$ (carbonate linkage)

$R^3$ can be but is not limited to
H
or the $R^2$ and $R^3$ bearing atoms are connected via $-C(=O)C-$ (carbonate linkage)

$R^4$ can be, but is not limited to
H
$CH_3$
$(C_2-C_{12})$alkyl
$(C_1-C_{12})$alkenyl
$(C_1-C_{12})$akynyl
$(C_1-C_8)[(C_1-C_4)$alkoxy]alkyl
$(C_1-C_8)[C_1-C_4)$alkoxy]alkenyl
$(C_6-C_{10})$aryl-$(C_1-C_5)$alkyl
$(C_2-C_9)$heteroaryl-$(C_1-C_5)$alkyl
$C(=O)-R^6$
$S(=O)_k(C_1-C_{12})$alkyl S(=O)$_k$(C$_1$-C$_{12}$)alkenyl
S(=O)$_k$(C$_1$-C$_{12}$)alkinyl
S(=O)$_k$(C$_6$-C$_{10}$)aryl
S(=O)$_k$(C$_2$-C$_9$)heteroaryl wherein k is 0, 1, 2, and alkyl, alkenyl, alkynyl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxy, nitro, cyano, azido, mercapto, —NR$^7$R$^7$, R$^7$C(=O)—, R$^7$C(=O)O—, R$^7$OC(=O)O—, R$^7$NHC(=O)—, R$^7$C(=O)NH—, R$^7$R$^8$NC(=O)—, R$^7$OC(=O)—, and -xNO$_2$ with x=O;S;N R$^5$ can be, but is not limited to
H
CH$_3$
C(=O)—R$^6$
R$^6$ can be, but is not limited to
Amino acid
CH$_3$
(C$_2$-C$_{12}$)alkyl
(C$_1$-C$_{12}$)alkenyl
(C$_1$-C$_{12}$)akynyl
(C$_1$-C$_8$)[(C$_1$-C$_4$)alkoxy]alkyl
(C$_1$-C$_8$)[C$_1$-C$_4$)alkoxy]alkenyl
(C$_6$-C$_{10}$)aryl-(C$_1$-C$_5$)alkyl
(C$_2$-C$_9$)heteroaryl-(C$_1$-C$_5$)alkyl
(CH$_2$)$_k$COO(CH$_2$)$_k$H
(CH$_2$)$_k$O(CH$_2$)$_k$COO(CH$_2$)$_k$H
CH=CHC(=O)OH wherein k is 1-10 and k' 0, 1 or 2.

R$^7$, R$^8$ can be independently, but are not limited to
H
(C$_1$-C$_{10}$)alkyl
(C$_1$-C$_{10}$)alkenyl
(C$_1$-C$_{10}$)akynyl
(C$_1$-C$_8$)[(C$_1$-C$_4$)alkoxy]alkyl
(C$_1$-C$_8$)[C$_1$-C$_4$)alkoxy]alkenyl
(C$_6$-C$_{10}$)aryl-(C$_1$-C$_5$)alkyl
(C$_2$-C$_9$)heteroaryl-(C$_1$-C$_5$)alkyl wherein alkyl, alkenyl, alkynyl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxy, nitro, cyano, azido, and -xNO$_2$ with x=O;S;N or N(R$^7$R$^8$) is an aziridine, azetidine, pyrrolidine, piperidine, azepane or azocane, 1-substituted piperazine, or morpholine moiety R$^9$ can be, but is not limited to:
Halogen
(C$_1$-C$_3$)alkyl
NO$_2$
CN
OCH$_3$
N(CH$_3$)$_2$
N$_3$
SH
S(C$_1$-C$_4$)alkyl;

may be rendered more soluble by preparation as a salt of: acetic, formic, propionic, suberic, malic, citric, maleic, fumaric, succinic, azelaic, pyruvic, alpha ketoglutaric, aspartic, glutamic, sulfonic and ascorbic acid.

Similarly, a compound family such as the following:

R1 can be but is not limited to
H, P(=O)(OH)$_2$, S(=O)$_2$(OH), saccharide, C(=O)—R$^7$,
CH$_3$
(C$_2$-C$_{12}$)alkyl
(C$_1$-C$_{12}$)alkenyl
(C$_1$-C$_{12}$)akynyl
(C$_1$-C$_8$)[(C$_1$-C$_4$)alkoxy]alkyl
(C$_1$-C$_8$)[C$_1$-C$_4$)alkoxy]alkenyl
(C$_6$-C$_{10}$)aryl-(C$_1$-C$_5$)alkyl
(C$_2$-C$_9$)heteroaryl-(C$_1$-C$_5$)alkyl
NO$_2$
S(=O)$_k$(C$_1$-C$_{10}$)alkyl
S(=O)$_k$(C$_1$-C$_{10}$)alkenyl
S(=O)$_k$(C$_1$-C$_{10}$)alkynyl
S(=O)$_k$(C$_6$-C$_{10}$)aryl
S(=O)$_k$(C$_2$-C$_9$)heteroaryl wherein k is 0, 1 or 2, and alkyl, alkenyl, alkynyl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxy, nitro, cyano, azido, mercapto, —NR$^8$R$^9$, R$^8$C(=O)—, R$^8$C(=O)O—, R$^8$OC(=O)O—, R$^8$NHC(=O)—, R$^8$C(=O)NH—, R$^8$R$^9$NC(=O)—, R$^8$OC(=O)—, and -xNO$_2$ with x=O;S;N R$^2$ can be, but is not limited to
H
—NO$_2$
C(=O)—R$^6$
O-(aryl-R$^{10}$)
or the R$^2$ and R$^3$ bearing atoms are connected via —C(=O)C— (carbonate linkage)

R$^3$ can be but is not limited to
H
or the R$^2$ and R$^3$ bearing atoms are connected via —C(=O)C— (carbonate linkage)

R$^4$ can be, but is not limited to
H
CH$_3$
(C$_2$-C$_{12}$)alkyl
(C$_1$-C$_{12}$)alkenyl
(C$_1$-C$_{12}$)akynyl
(C$_1$-C$_8$)[(C$_1$-C$_4$)alkoxy]alkyl
(C$_1$-C$_8$)[C$_1$-C$_4$)alkoxy]alkenyl
(C$_6$-C$_{10}$)aryl-(C$_1$-C$_5$)alkyl
(C$_2$-C$_9$)heteroaryl-(C$_1$-C$_5$)alkyl
C(=O)—R$^6$
S(=O)$_k$(C$_1$-C$_{12}$)alkyl
S(=O)$_k$(C$_1$-C$_{12}$)alkenyl
S(=O)$_k$(C$_1$-C$_{12}$)alkinyl
S(=O)$_k$(C$_1$-C$_{12}$)alkinyl S(=O)$_k$(C$_6$-C$_{10}$)aryl
S(=O)$_k$(C$_2$-C$_9$)heteroaryl wherein k is 0, 1, 2, and alkyl, alkenyl, alkynyl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxy, nitro, cyano, azido, mercapto, —NR$^8$R$^9$, R$^8$C(=O)—, R$^8$C(=O)O—, R$^8$OC(=O)O—, R$^8$NHC(=O)—, R$^8$C(=O)NH—, R$^8$R$^9$NC(=O)—, R$^8$OC(=O)—, and -xNO$_2$ with x=O;S;N R$^5$ can be, but is not limited to
H
CH$_3$
C(=O)—R$^7$
R6=R1
R$^7$ can be, but is not limited to
Amino acid
CH$_3$
(C$_2$-C$_{12}$)alkyl
(C$_1$-C$_{12}$)alkenyl
(C$_1$-C$_{12}$)akynyl
(C$_1$-C$_8$)[(C$_1$-C$_4$)alkoxy]alkyl
(C$_1$-C$_8$)[C$_1$-C$_4$)alkoxy]alkenyl
(C$_6$-C$_{10}$)aryl-(C$_1$-C$_5$)alkyl
(C$_2$-C$_9$)heteroaryl-(C$_1$-C$_5$)alkyl
(CH$_2$)$_k$COO(CH$_2$)$_k$H
(CH$_2$)$_k$(O(CH$_2$)$_k$(COO(CH$_2$)$_k$H
CH=CHC(=O)OH wherein k is 1-10 and k' 0, 1 or 2.

R$^8$, R$^9$ can be independenty, but are not limited to
H
(C$_1$-C$_{10}$)alkyl
(C$_1$-C$_{10}$)alkenyl
(C$_1$-C$_{10}$)akynyl
(C$_1$-C$_8$)[C$_1$-C$_4$)alkoxy]alkyl
(C$_1$-C$_8$)[C$_1$-C$_4$)alkoxy]alkenyl
(C$_6$-C$_{10}$)aryl-(C$_1$-C$_5$)alkyl
(C$_2$-C$_9$)heteroaryl-(C$_1$-C$_5$)alkyl wherein alkyl, alkenyl, alkynyl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxy, nitro, cyano, azido, and -xNO$_2$ with x=O;S;N or N(R$^7$R$^8$) is an aziridine, azetidine, pyrrolidine, piperidine, azepane or azocane, 1-substituted piperazine, or morpholine moiety R$^{10}$ can be, but is not limited to:
Halogen
(C$_1$-C$_3$)alkyl
NO$_2$
CN
OCH$_3$
N(CH$_3$)$_2$
N$_3$
SH
S(C$_1$-C$_4$)alkyl;

may be rendered more soluble soluble by preparation as a salt of: acetic, formic, propionic, suberic, malic, citric, maleic, fumaric, succinic, azelaic, pyruvic, alpha ketoglutaric, aspartic, glutamic, sulfonic and ascorbic acid.

Increased solubility via conjugation with solubility enhancing groups

The solubility of the azilides can be improved by the addition of polar groups via a reactive site. Preferred reactive sites are the 2' OH and the 11OH. Addition of polar groups to these sites provides for a compound of the following formula:

in which
R1=H, P(=O)(OH)$_2$, S(=O)$_2$(OH), a saccharide or C(=O)—R4, wherein R4=(CH$_2$)$_2$—C(=O)OH, C(=O)CH=CHC(=O)OH, CH=CHC(=O)OH, or an amino acid;
R2=H, C(=O)(CH$_2$)$_2$C(=O)H, or a saccharide moiety
or a pharmaceutically acceptable salt or formaldehyde adduct thereof.

A compound of the following formula:

in which
R1=H, acetyl or C(=O)(CH$_2$)$_2$C(=O)OH;
R2=H or C(=O)(CH$_2$)$_2$C(=O)OH [C(=O)(CH$_2$)$_2$C(=O)OH only in case that R1 is C(=O)(CH$_2$)$_2$C(=O)OH];
or a pharmaceutically acceptable salt or formaldehyde adduct thereof.

A compound of the following formula:

wherein
R1=H, P(=O)(OH)$_2$, S(=O)$_2$(OH), a saccharide or C(=O)—R3, wherein R3=(CH$_2$)$_2$—C(=O)OH or an amino acid;

or a pharmaceutically acceptable salt or formaldehyde adduct thereof

Thus, in one aspect, the invention provides compounds according to the formulae herein, and salts thereof.

In another aspect, this invention features a method for treating an autoimmune, inflammatory, transplant, pulmonary, COPD, respiratory, bronchial, diabetic or related disease including the signs and symptoms of common cold, rhinitis and asthma. The method includes administering to a subject in need thereof an effective amount of a compound described herein. Optionally, the method includes co-usage with other anti-inflammatory agents or therapeutic agents. The use of the compounds described herein exerts a positive effect in part because of their facile uptake into cells.

In a preferred embodiment, the disease to be treated is an inflammatory disease of the lungs or airways. In a further preferred embodiment, the disease to be treated is airway inflammation associated with viral infection, asthma, COPD, diffuse panbronchiolitis, chronic sinusitis, cystic fibrosis and chronic bronchitis In another preferred embodiment, the disease to be treated is metabolic disease such as diabetes. In a still further preferred embodiment, the disease to be treated is Type II diabetes.

In another preferred embodiment, the disease to be treated is a degenerative disease of the muscles, lungs or brain characterized by pathological activation of immune cells.

To treat the disease, the macrocycle is administered to a patient in need at a dose of between 0.1 and 100 µmol/kg via a suitable route and formulation. Administration of the compound is continued for as long as necessary. Under some circumstances, the initial dose will be higher than the subsequent doses.

Formulating the macrocycle in a pharmaceutically acceptable dosage form provides for a method of treating the patient such that signs of excess immune system activity are reduced. In a preferred embodiment, the macrocycle is formulated for oral administration. In another embodiment, the macrocycle is formulated with enteric protection to provide for release in the lower abdominal tract. Another embodiment, the macrocycle is formulated for delayed release or slow release in addition to enteric coating.

In a preferred embodiment, the macrocycle is rendered more soluble by formation of a salt with an organic acid, preferably ascorbic acid and administered either orally or by inhalation or intranasally.

Definitions

The term "cyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms. The term "heterocyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms having one or more heteroatoms, such as S, O, or N in each ring.

The term saccharide refers to any unprotected and protected natural and non-natural D- or L- and alpha or beta aldoses or ketoses, any deoxygenated, amino- or thio variants of them, and any possible oligomeric combinations. Protective groups can be but are not limited to acetyl, benzyl, allyl, silyl.

The term "amino acid" refers to organic compounds containing at least one amino group (NH$_2$), and at least one carboxylic acid group (COOH), and any of various side groups, especially any of the 20 compounds that have the basic formula NH$_2$CHRCOOH.

The term organic acid refers to an acidic molecule that contains at least one carbon and an acidic function.

The terms "halogen" and "halo" refer to radicals of fluorine, chlorine, bromine or iodine. The term "macrolactone" or "macrocycle" refers to a large lactone ring (i.e., cyclic ester) having at least 10 ring atoms. The term "macrolide" refers to a chemical compound characterized by a large lactone ring (having at least 10 ring atoms) containing one or more keto and hydroxyl groups, or to any of a large group of antibacterial antibiotics containing a large lactone ring linked glycosidically to one or more sugars; they are produced by certain species of *Streptomyces* and inhibit protein synthesis by binding to the 50S subunits of 70S ribosomes. Examples include erythromycin, azithromycin (compound 3), and clarithromycin. The term "ketolide" refers to a chemical compound characterized by a large lactone ring (having at least 10 ring atoms) containing one or more keto groups.

The term "alkyl" (or "alkenyl" or "alkynyl") refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. Alkenyl groups and alkynyl groups have one or more double or triple carbon-carbon bonds, respectively, in the chain. Unless otherwise stated, an alkyl group has from 1 to 10 carbon atoms, or from 1 to 6 carbon atoms. Similarly, unless otherwise stated, an alkenyl group or alkynyl group has from 2 to 10 carbon atoms, or from 2 to 6 carbon atoms. In certain embodiments, an alkyl group is a methyl, ethyl, propyl, or isopropyl group.

The term "aryl" refers to a hydrocarbon ring system (monocyclic or bicyclic) having the indicated number of carbon atoms and at least one aromatic ring. Examples of aryl moieties include, but are not limited to, phenyl, naphthyl, and pyrenyl.

The term "heteroaryl" refers to a ring system (monocyclic or bicyclic) having the indicated number of ring atoms including carbon atoms and at least one aromatic ring. The ring system includes at least one heteroatom such as O, N, or S (e.g., between 1 and 4 heteroatoms, inclusive, per ring) as part of the ring system. Examples of heteroaryl moieties include, but are not limited to, pyridyl, furyl or furanyl, imidazolyl, benzimidazolyl, pyrimidinyl, thiophenyl or thienyl, quinolinyl, indolyl, and thiazolyl.

The term "alkoxy" refers to an —O-alkyl radical.

The term "cycloalkyl" refers to a non-aromatic hydrocarbon ring system (monocyclic or bicyclic), containing the indicated number of carbon atoms.

The term "heterocycloalkyl" refers to a non-aromatic ring system (monocyclic or bicyclic), containing the indicated number of ring atoms including carbon atoms and at least one heteroatom such as O, N, or S (e.g., between 1 and 4 heteroatoms, inclusive, per ring) as part of the ring system.

Such an example is seen in cardiovascular diseases such as atherosclerosis where there is a strong inflammatory component to the events that result in the thickening and fragmentation of the plaque. This inflammation may be effectively reduced by the application of a range of agents that interact with the macrophage class.

Reference to atoms like hydrogen or carbon also includes their isotopes deuterium and Carbon 13.

The compounds described herein include the compounds themselves, as well as their salts, if applicable. Such salts, for example, can be formed between a positively charged substituent (e.g., amino) on a compound and an anion. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Furthermore, the aforementioned compounds also include their N-oxides. The term "N-oxides" refers to one or more nitrogen atoms, when present in a compound, are in N-oxide form, i.e., N→O.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

The present invention also features a pharmaceutical composition including at least one compound of this invention and a pharmaceutically acceptable carrier. Optionally, the pharmaceutical composition includes one or more other therapeutic agents.

This invention further features a method for making any of the compounds described above. The method includes taking any intermediate compound delineated herein, reacting it with any one or more reagents to form a compound of this invention including any processes specifically delineated herein.

Also within the scope of this invention are compositions having one or more of the compounds of this invention for use in treating various diseases described above, and the use of such a composition for the manufacture of medication for the just-described use.

Other advantages, objects, and features of the invention will be apparent from the description and drawings, and from the claims.

To practice the method of treating a disease, the compounds of this invention can be administered to a patient, for example, in order to treat a disease described above. The compound can, for example, be administered in a pharmaceutically acceptable carrier such as physiological saline, in combination with other therapeutic agents, and/or together with appropriate excipients. The compound described herein can, for example, be administered by injection, intravenously, intra-arterially, subdermally, intraperitoneally, intramuscularly, or subcutaneously; or orally, buccally, nasally, transmucosally, topically, in an ophthalmic preparation, by inhalation, by intracranial injection or infusion techniques, with a dosage ranging from about 0.1 to about 20 mg/kg of body weight, preferably dosages between 10 mg and 1000 mg/dose, every 4 to 120 hours, or according to the requirements of the particular therapeutic agent. The methods herein contemplate administration of an effective amount of compound or compound composition to achieve the desired or stated effect. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, therapeutic agent combination, the severity and course of the disease, condition or symptoms, the patient's disposition to the disease, condition or symptoms, and the judgment of the treating physician.

Pharmaceutical compositions of this invention comprise a compound of this invention or a pharmaceutically acceptable salt thereof; and any pharmaceutically acceptable carrier, adjuvant or vehicle. Such compositions may optionally comprise additional therapeutic agents. The compositions delineated herein include the compounds of the formulae delineated herein, as well as additional therapeutic agents if present, in amounts effective for achieving a modulation of a disease.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying therapeutic agent delivery systems (SEDDS) such as D-alpha-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, polyethylene glycol and wool fat. Cyclodextrins such as I-, σ-, and K-cyclodextrin, or chemically modified derivatives such as hydroxyalkyl cyclodextrins, including 2- and 3-hydroxypropyl-σ-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A suitable in vitro assay can be used to preliminarily evaluate a compound of this invention in treating a disease. In vivo screening can also be performed by following procedures well known in the art. See, e.g., the specific examples below.

Additional References

Axton et al., 1992, J. Chem. Soc. Perkin Trans. I 2203 ff.
Bartlett et al., 1991, Agents and Actions, 32 10-21.
Benslay D N and Bendele A M, 1991, Agents Actions 34: 254.
Billingham et al., 1954. Proc. R. Soc. 143: 43-55.
Bright et al. J. Antibiotics, 41 (1988), 1029
Bosnar, et al., 2009. Azithromycin and clarithromycin inhibit lipopolysaccharide-induced murine pulmonary neutrophilia mainly through effects on macrophage-derived granulocyte-macrophage colony-stimulating factor and interleukin-1beta. J. Pharmacol. Exp. Ther. 331, 104-113.
Hutchins R O, Hoke D, Keogh J, Koharstki D, 1969, Sodium Borohydride in Dimethyl Sulfoxide or Sulfolane. Convenient Systems for Selective Redutions of Primary, Secondary, and Certain Tertiary Halides and Tosylates. Tetrahedron Letters, 3495-3498.
Ianaro et al., 2000, Anti-inflammatory activity of Macrolide Antibiotics. J. Pharmacol. Ex. Therapeutics. 292:156-161.
Labro M T and Abdelghaffar H, 2001, Immunomodulation by macrolide antibiotics. J. Chemother. Feb.; 13(1):3-8. Review.
Labro M T, 1998, Anti-inflammatory activity of macrolides: a new therapeutic potential? J. Antimicrobial Chemother. 41, Suppl., 37-46.
Laufen et al., Drug Res. 40 (1990), 686.
Mencarelli A, et al., Development of non-antibiotic macrolide that corrects inflammation-driven immune dysfunction in models of inflammatory bowel diseases and arthritis. Eur J Pharmacol. 2011 Aug. 31; 665(1-3):29-39.
Murphy et al., Azithromycin alters macrophage phenotype. J Antimicrob Chemother. 2008 March; 61(3):554-60. Epub 2008 Jan. 29. PubMed PMID: 18230686
Quallich L G, Greenson J, Haftel H M, Fontana R J, 2001, Is it Crohn's disease? A severe systemic granulomatous reaction to sulfasalazine in patient with rheumatoid arthritis, BMC Gastroenterol; 1(1):8.
Rapp, Ann Pharmacotherap. 32 (1998), 785; b)
Rubin B K, Henke M O Immunomodulatory activity and effectiveness of macrolides in chronic airway disease. Chest. 2004 Feb.; 125(2 Suppl):70S-78S. Review. PubMed PMID: 14872003.
Saint-Criq et al., Azithromycin fails to reduce inflammation in cystic fibrosis airway epithelial cells. Eur J Pharmacol. 2012 Jan. 5; 674(1):1-6. j.ejphar.2011.Oct. 27. Epub 2011 Oct. 26.
Saint-Criq et al., Restoration of chloride efflux by azithromycin in airway epithelial cells of cystic fibrosis patients. Antimicrob Agents Chemother. 2011 Apr.; 55(4):1792-3. Epub 2011 Jan. 10. (B)
Schultz, M. J., 2004. Macrolide activities beyond their antimicrobial effects: macrolides in diffuse panbronchiolitis and cystic fibrosis. J. Antimicrob. Chemother. 54, 21-28.
Schönfeld, et al., (Eds.), Macrolide Antibiotics, Birkhauser, Basel 2002, p. 101 lit. cit. 3), p. 87
Schroit A J, Madsen J, Nayar R, 1986, Liposome-cell interactions: in vitro discrimination of uptake mechanism and in vivo targeting strategies to mononuclear phagocytes, Chem Phys Lipids. Jun.-Jul.; 40(2-4):373-93.
Shinkai M, Henke M O, Rubin B K. Macrolide antibiotics as immuno-modulatory medications: proposed mechanisms of action. Pharmacol Ther. 2008 Mar.; 117(3): 393-405. Epub 2007 Dec. 15. Review. PubMed PMID: 18289694
Yanagihara et al., Diffuse panbronchiolitis--pathophysiology and treatment mechanisms. Int J Antimicrob Agents. 2001; 18 Suppl 1:S83-7.

Patents and Pending Patent Applications:

| | | |
|---|---|---|
| PCT03/070173 | February 2002 | Burnet et al |
| U.S. Ser. No. 61/391,679 | October 2010 | Burnet et al |
| U.S. Pat. No. 4,328,334 | May 1982 | Kobrehel et al. |
| U.S. Pat. No. 3,478,014 | November 1969 | Djokic et al. |

-continued

| U.S. Pat. No. 3,652,537 | March 1972 | Massey |
| U.S. Pat. No. 4,988,677 | January 1991 | Franco |
| U.S. Pat. No. 5,543,400 | August 1996 | Agouridas |
| US2001/0053782 | December 2000 | Blumenkopf et al. |
| PCT03/070254A1 | February 2002 | Burnet et al. |
| WO2004029067 | February 2003 | Berdik et al. |
| WO09/963937 | July 1999 | Griffin |
| EP0283055 | September 1988 | Carevic and Djokic |
| EP0627406A1 | October 1992 | Fujita et al. |

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following examples. It should be understood that these examples are for illustrative purposes only and are not to be construed as limiting this invention in any manner.

EXAMPLES

Unless otherwise specified, all commercially available reagents and solvents were used without further purification. All Chemical names and structures were generated from ChemDraw Ultra (Cambridge Soft).

Example 1

Compound 1

A stirred solution of 27 ml (314 mmol) oxalylchloride in ultradry DCM (700 ml) under argon was chilled to −73° C.±3° C. in an acetone-dry ice-bath. A solution of 27 ml (380 mmol) ultradry dimethylsulfoxide in 100 ml of ultradry DCM was added slowly (60 min total addition time) through a dropping funnel. Initially a vigorous gas evolution was observed with every drop. The solution was stirred at −73° C.±3° C. for 10 more min A solution of 3-De(2,6-dideoxy-3-C-methyl-3-O-methyl-α-L-ribohexopyranosyl-oxy)-3-oxy-azithromycin 2'-O-acetate (U.S. Pat. No. 6,369,035) (40 g, 63.2 mmol, dried for 3 hours in high vacuum at 60° C.) in dry DCM (220 ml) was directly filtered into the separation funnel and added slowly (2 hours total addition time) in order to keep the temperature below −70° C. A colourless suspension was obtained. Then 100 ml (584 mmol) of ultradry ethyl DIPEA were added slowly (60 min total addition time) through a dropping funnel, which furnished a clear yellowish solution. The reaction mixture was stirred for another 20 min at −73° C.±3° C., subsequently followed by addition of 20 ml MeOH in a single portion. The solution was allowed to reach room temperature. Then the reaction mixture was transferred into a separation funnel and the reaction flask washed with additional DCM (150 ml). The combined organic layers were washed with a mixture of brine (1000 ml) and a 50 wt % solution of NaOH in water (80 ml).

The organic layer was washed one more time with brine (1000 ml), then dried over $Na_2SO_4$ and evaporated under reduced pressure.

MeOH (500 ml) was added to the orange oil and the solution was stirred at room temperature over night. After the reaction mixture has been checked for completion by TLC, the solvent was removed under reduced pressure and the orange oil taken up into 700 ml of DCM. The organic layer was extracted with a mixture of 500 ml brine and 300 ml of saturated bicarbonate. The separation of the layers was allowed to proceed over night. Subsequently the organic layer was dried over $Na_2SO_4$. The solvent was removed under reduced pressure and the residue was dissolved in 80 ml of boiling EtOAc. The solution was allowed to cool down to room temperature. In order to complete the precipitation the suspension was kept at −20° C. over night. Crystals were isolated and washed with some EtOAc at −20° C. The product (compound 1) was dried in high vacuum for 4 hours.

Example 2

Compound 2

Method a:
Obtained as intermediate during the synthesis of compound 1
Method b:
Starting from compound1:
To a stirred solution of compound 1 (300 mg; 0.51 mmol) in dry DCM (3.0 mL) was added $Ac_2O$ (51 µL, 0.53 mmol) at room temperature. The mixture was stirred at room temperature overnight. $K_2CO_3$ (230 mg) was added. After stirring at room temperature for 20 min the solid was filtered off and washed with DCM. The combined filtrates were concentrated to dryness; the crude product was purified by column chromatography (eluent: $CHCl_3$/iso-propanol/$NH_3$ 7M in MeOH 30:1:1) to yield 184 mg of the title compound.

Example 3

Compound 3

To as stirred solution of Compound 1 (2.00 g, 3.4 mmol) in dry DCM (20 mL) were added at room temperature succinic anhyde (377 mg, 3.74 mmol) and a catalytic amount of DMAP. The mixture was stirred at room temperature for 30 min and concentrated to dryness (contaminated with compound 1).

Example 4

Compound 4

Carbonyldiimidazole (28 mg, 0.17 mmol, 0.5 eq.) Dicyclohexylcarbodiimide (56 mg, 0.27 mmol, 0.8 eq.) were combined in a round bottom flask and diluted with THF (1.3 mL). The mixture was stirred at room temperature for 1 h at which point compound 1 (200 mg, 0.34 mmol) and fumaric acid (40 mg, 0.34 mmol) were added as solid to the reaction mixture. The reaction mixture turned reddish in color and produced a lot of precipitate. Reaction was allowed to stir at room temperature overnight. The precipitate was removed by filtration and the filtrate evaporated in vacuo. The reddish compound obtained showed in MS: M+687 and used without further purification.

Example 5

Compound 5

Compound 1 (120 mg) was dissolved in dry DMF (3.0 mL). $SO_3*N(Et)_3$ (220 mg) was added and the mixture was warmed to 55° C. for 12 h with stiffing. Silica gel (3.0 g) were applied, and the mixture was concentrated to dryness in a fine vacuum with gentle warming. The preparation was chromatographed with cyclohexane/acetone/methanol 6/3/2 mixture (containing 0.5% of TEA). The fractions containing the target compound (indicated by MS: [m+H$^+$]/z=669) were combined and concentrated to dryness to yield 49 mg. The material was completely water soluble. A minute hydrophobic contamination can be removed by passing through a C-18 SPE column Example 6

Compound 6

Fmoc-L-Val-OH (37 mg, 0.12 mmo), EDCI*HCl (42 mg, 0.22 mmol), and HOBt*$H_2O$ (30 mg, 0.22 mmol) were suspended in dry dichloromethane (2 mL) at room temperature. DIPEA (37 μL, 0.22 mmol) was added and the mixture was stirred at room temperature for 5 min. Afterwards compound1 (71 mg, 0.12 mmol) was added in one portion. The reaction mixture was stirred at room temperature overnight. DCM and sodium bicarbonate solution (sat.) were added; after extraction the organic phase is washed with brine (1×), dried with Na$_2$SO4 and concentrated to dryness. The rude product contains also starting material.

To the crude product (10 mg) was added a solution of piperidine in DMF (20 Vol %, 400 μL). The mixture was shaken at room temperature for 40 min MS showed Fmoc cleavage.

Example 7

Compound 7 and Compound 8

Compound 1 (147 mg, 0.25 mmol), acetobromoglucose (100 mg, 0.25 mmol), and TEA (52 μL, 0.375) were dissolved in dry DCM (2 mL) at room temperature under argon atmosphere. To this solution was added Montmorillonite K10 (15 mg). The mixture was sonicated at room temperature overnight (water temperature raised to 45° C.; solvent evaporated). Dry DCM was added and the mixture was kept at room temperature for another day without sonication and another two days in the freezer. DCM was added and the catalyst was filtered off. The filtrate is concentrated to dryness.

The crude product contains—according to MS—besides starting materials the compounds 7 and 8.

Example 8

Reaction of Compound 1 with Formaldehyde 250 mg of the title compound was dissolved in DMF (5 mL), and formaldehyde was bubbled (from thermal decomposition of paraformaldehyde with a gentle stream of argon) through the solution. The progress of the reaction was monitored by MS. When all starting material was consumed ([M+H+]/z=589 changes to 619), the solvent was evaporated (0.5 mbar, 60° C.). Higher hydroxymethylated species were removed by chromatography (cyclohexane/acetone 2/1, containing 0.5% of triethylamine) over silica gel. yield 200 mg.

Example 9

Compound 9

Fmoc-L-Val-OH (37 mg, 0.12 mmo), EDCI*HCl (42 mg, 0.22 mmol), and HOBt*$H_2O$ (30 mg, 0.22 mmol) were suspended in dry dichloromethane (2 mL) at room temperature. DIPEA (37 μL, 0.22 mmol) was added and the mixture was stirred at room temperature for 5 min. Afterwards azithromycin (90 mg, 0.12 mmol) was added in one portion. The reaction mixture was stirred at room temperature overnight. DCM and sodium bicarbonate solution (sat.) were added; after extraction the organic phase is washed with brine (1×), dried with Na$_2$SO$_4$ and concentrated to dryness. The crude product contains besides coupling product predominantly starting material.

To the crude product (10 mg) was added a solution of piperidine in DMF (20 Vol %, 400 μL). The mixture was shaken at room temperature for 40 min MS showed Fmoc cleavage.

Example 10

Compound 10

Azithromycin (374 mg, 0.5 mmol) and acetobromoglucose (200 mg, 0.49 mmol) were dissolved in dry DCM (5 mL) at room temperature under argon atmosphere. To this solution was added Montmorillonite K10 (25 mg). The mixture was stirred at room temperature overnight and kept at room temperature without stirring for another 4 days. DCM was added and the catalyst was filtered off. The filtrate was concentrated to dryness. The crude product contained—according to MS—besides starting materials the desired product (compound 10).

Example 11

Compound 11

Azithromycin (494 mg, 0.66 mmol), maleic anhydride (71 mg, 0.73 mmol), and DMAP (catalytic amount) were dissolved in dry DCM (4 mL), stirred at room temperature overnight and concentrated to dryness. The crude product contained—according to MS—besides starting materials the desired product.

Example 12

Compound 12

1.0 g of compound 1 (1.6 mmol) and triethylamine (337 μl, 2.4 mmol) were dissolved in dry DCM (10 ml). The mixture was cooled to 0° C. and methanesulfonyl chloride (138 μl, 1.8 mmol) was added in one portion. The reaction mixture was allowed to warm to room temperature. After 30 min DCM and sodium bicarbonate solution (sat.) were added; after extraction the organic phase was dried ($Na_2SO_4$) and concentrated to dryness to give the product (compound 12) (907 mg) as white foam.

Example 13

Compound 12 (420 mg, 0.68 mmol) was dissolved in dry MeOH (20 mL) at room temperature and stirred overnight. The mixture was taken up in DCM, washed with sodium bicarbonate solution (sat.) (1 x), with brine (1 x), was dried (sodium sulfate), and was concentrated in vaccuo to give compound 13 as a white solid (quantitative yield).

Example 14

Compound 13 (150 mg, 0.26 mmol), succinic anhydride (29 mg, 0.29 mmol) and a catalytic amount of DMAP were dissolved in dry DCM (1.00 mL) at room temperature The mixture was stirred at room temperature overnight and concentrated to dryness to yield compound 14 besides some starting material (some compound 15 present).

Example 15

Compound 13 (150 mg, 0.26 mmol), succinic anhydride (29 mg, 0.29 mmol) and a catalytic amount of DMAP were dissolved in dry DCM (1.00 mL) at room temperature The mixture was stirred at room temperature overnight and concentrated to dryness to yield compound 15 besides some starting material material (some compound 14 present).

Example 16

Maximum Solubility Determination of Organic Salts in Saline

The macrolide was taken up in saline (0.9% aq. NaCl solution) and an acid equivalent of the organic acid was added (if more than one mole of acid was present per mole of compound, it was assumed that each group had the same equivalence). The resulting mixture was agitated overnight and, when needed underwent sonication. The mixtures were given a visual score depending on the presence of precipitate in the mixture (Score ranges from 0 to 4, with 0 showing undissolved solid precipiate and 4 being fully-dissolved). The results for some of the salts are shown in Table 1 below. Solubility of the salts was tested in 10 mM, 100 mM, 500 mM and 1M.

TABLE 1

Comparison of pH Values and Visual Score for some organic salts.

| | Concentration in Saline | | | | | | | |
|---|---|---|---|---|---|---|---|---|
| | 10 mM | | 100 mM | | 500 mM | | 1M | |
| Organic Acid | pH | Visual Score | pH | Visual Score | pH | Visual Score | pH | Visual Score |
| citric acid | 6.0 | 4 | 7.0 | 4 | 6.0 | 4 | 9.0 | 4 |
| glutaric acid | 5.9 | 4 | 7.0 | 4 | 7.5 | 4 | 9.5 | 1 |
| maleic acid | 6.9 | 4 | 7.0 | 4 | 9.0 | 4 | 10.0 | 1 |

TABLE 1-continued

Comparison of pH Values and Visual Score for some organic salts.

| | Concentration in Saline | | | | | | | |
|---|---|---|---|---|---|---|---|---|
| | 10 mM | | 100 mM | | 500 mM | | 1M | |
| Organic Acid | pH | Visual Score | pH | Visual Score | pH | Visual Score | pH | Visual Score |
| fumaric acid | 4.7 | 4 | 6.5 | 4 | 5.5 | 4 | 2.0 | 4 |
| ascorbic acid | 4.9 | 4 | 6.0 | 4 | 6.0 | 4 | 6.0 | 4 |
| pyruvic acid | 2.9 | 4 | 8.0 | 4 | 8.5 | 4 | 5.0 | 4 |
| aspartic acid | 8.5 | 2 | 6.0 | 4 | 6.0 | 4 | 8.0 | 1 |
| subaric acid | 6.8 | 4 | 5.5 | 4 | 8.0 | 4 | 10.0 | 2 |
| 2-ketoglutaric acid | 5.4 | 4 | 6.0 | 4 | 7.0 | 4 | 9.0 | 4 |
| oxaloacetatic acid | 7.1 | 4 | 8.0 | 4 | 9.0 | 4 | | |

Example 17

Maximum Solubility Determination of Inorganic Salts in Saline

The macrolide was taken up in saline (0.9% aq. NaCl solution) and an acidic equivalence of the inorganic acid was added. The resulting mixture was agitated overnight and when needed underwent sonification. The results are shown in Table 2.

TABLE 2

Comparison of pH Values and Visual Score for some inorganic salts.

| | 10 mM | |
|---|---|---|
| Inorganic Acid | Visual Score | pH |
| Hydrochloric acid | 1 | 8.6 |
| Sulfuric acid | 0 | 8.6 |
| Phosphoric acid | 0 | 8.7 |

Example 18

Titration of Macrolide with Organic Acid

The macrolide was taken up in saline (0.9% aq. NaCl solution) to a concentration of 10 mM and a solution of the organic acid in saline (10 mg/mL) was added in 100 μL increments. After each addition, the mixture or solution was placed in the ultrasonic bath for 10 minutes followed by agitation for an additional 10 minutes. The mixtures were given a visual score depending on the presence of precipitate in the mixture (0 to 4, 0 being undissolved and 4 being fully-dissolved) and the pH of the supernatant fluid was measured.

Table 3 shows the results of the titration and the minimum mole equivalence of acid needed to dissolve COMPOUND 1.

Table 4 shows the results of the titration and the minimum mole equivalence of acid needed to dissolve azithromycin.

TABLE 3

Titration results for 10 mM COMPOUND 1 in saline.

| Acid | Vol. Added (mL) Score = 4 | Amt acid added to dissolve (mg) | Amt corr. to mol eq. (mg) | mmole acid | mol. eq. acid | End conc. macrolide (mM) |
|---|---|---|---|---|---|---|
| Organic Salts | | | | | | |
| citric acid | 0.40 | 4.00 | 4.00 | 20.82 | 0.44 | 9.2 |
| glutaric acid | 0.40 | 4.00 | 4.00 | 30.28 | 0.58 | 9.3 |
| maleic acid | 0.40 | 4.00 | 4.00 | 35.38 | 0.81 | 9.2 |
| fumaric acid | 0.56 | 5.60 | 2.80 | 48.25 | 1.05 | 10.0 |
| ascorbic acid | 0.90 | 9.00 | 4.50 | 25.55 | 0.53 | 8.4 |
| pyruvic acid | 0.60 | 6.00 | 3.00 | 34.07 | 0.78 | 8.8 |
| aspartic acid | | 10.60 | 5.30 | 39.82 | 0.88 | 10.0 |
| subaric acid | | 8.30 | 8.30 | 47.65 | 1.05 | 10.0 |
| 2-ketoglutaric acid | 0.40 | 4.00 | 4.00 | 27.38 | 0.63 | 9.2 |
| oxaloacetatic acid | 0.40 | 4.00 | 4.00 | 30.29 | 0.64 | 9.2 |

TABLE 4

Titration results for azithromycin, 10 mM in saline

| Acid | Vol. Added (mL) Score = 4 | Amt acid added to dissolve (mg) | Amt corr. to mol eq. (mg) | mmole acid | mol. eq. acid | End conc. macrolide (mM) |
|---|---|---|---|---|---|---|
| Organic Salts | | | | | | |
| citric acid | 0.60 | 6.00 | 6.00 | 31.23 | 0.51 | 9.1 |
| glutaric acid | 0.60 | 6.00 | 6.00 | 45.41 | 0.75 | 9.1 |
| maleic acid | 0.60 | 6.00 | 6.00 | 53.06 | 1.00 | 9.0 |
| fumaric acid | | 4.40 | 4.40 | 37.91 | 0.74 | 10.0 |
| ascorbic acid | 0.80 | 8.00 | 4.00 | 22.71 | 0.41 | 8.7 |
| pyruvic acid | 0.60 | 6.00 | 3.00 | 34.07 | 0.66 | 9.0 |
| aspartic acid | | 10.20 | 5.10 | 38.32 | 0.70 | 10.0 |
| subaric acid | | 6.70 | 6.70 | 38.46 | 0.70 | 10.0 |
| 2-ketoglutaric acid | 0.60 | 6.00 | 6.00 | 41.06 | 0.76 | 9.0 |
| oxaloacetatic acid | 0.80 | 8.00 | 8.00 | 60.57 | 1.10 | 8.7 |

ABBREVIATIONS

DCM Dichloromethane
DIPEA N,N-Diisopropylethylamin;
MEOH Methanol
NaOH Sodium hydroxide
TLC Thin layer chromatography
DMAP 4-Dimethylaminopyridine
DMF Dimethylformamide
TEA Triethylamine
MS Mass spectrometry
EDCI*HC Ethyl-3-[3-dimethylaminopropyl]carbodiimide hydrochloride
HOBt*H$_2$O 1-Hydroxybenzotriazole Example 19

Liver Signs in Diabetes

Figure 1:
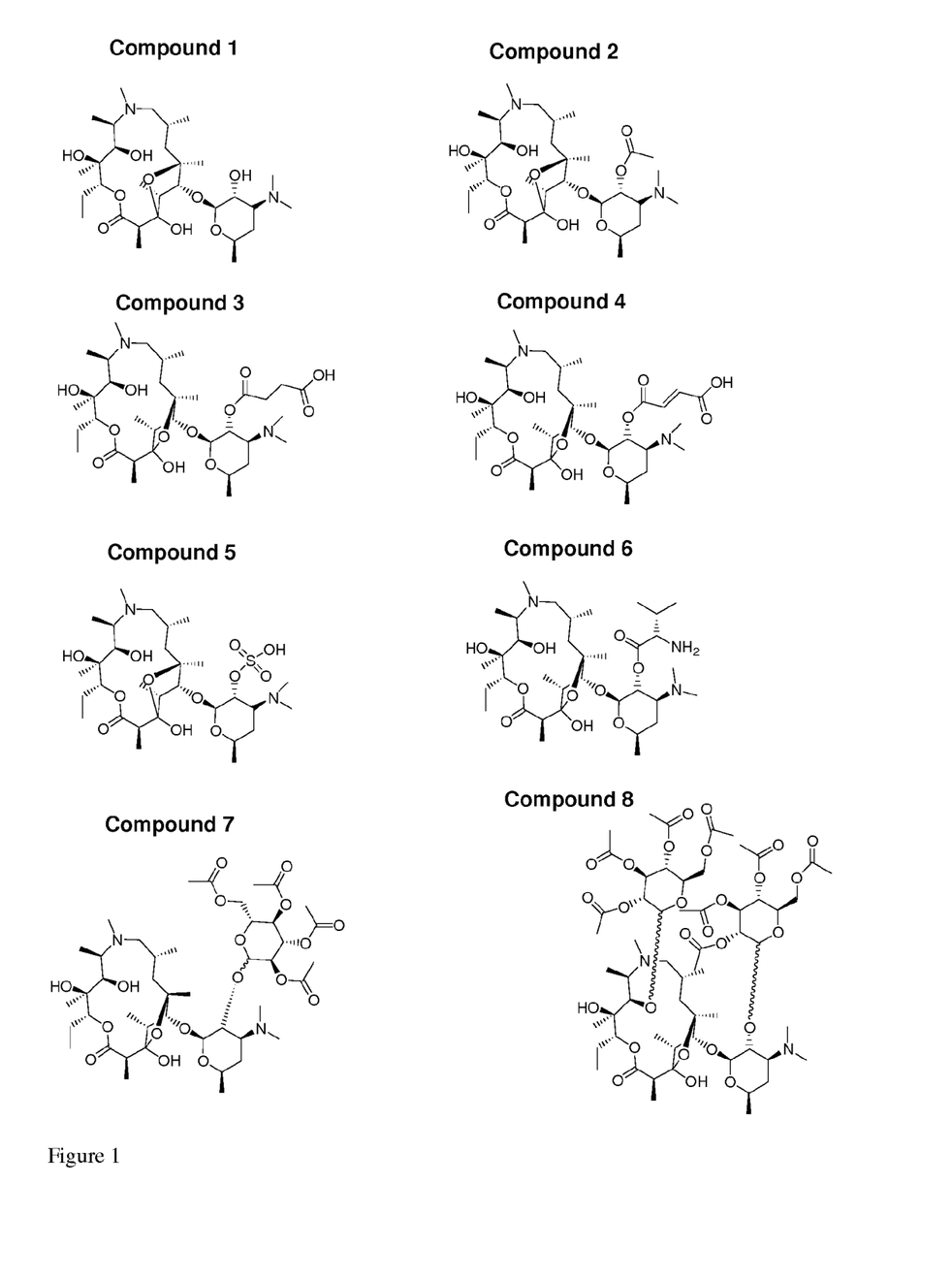
FIG. 1. Structures of the macrolides described herein
Figure 2:
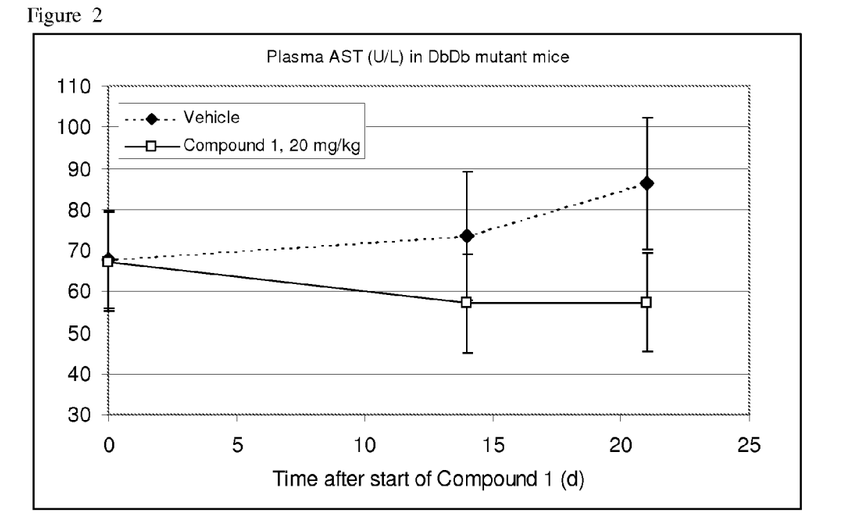
FIG. 2. Effect of compound 1 on release of liver enzymes into plasma

Diabetic mutant mice (DbDb) defective in leptin signaling are provided with either chow, or chow containing 20 mg of Compound 1 per 150 g chow. Animals are allowed to consume chow ad libitum. Each week a small blood sample is obtained from animals via the tail vein and liver enzyme levels are determined using a protocol based on standard methods for determination of AST and ALT (aspartate and alanine transaminase). Data following 3 weeks of drug treatment are reported in FIG. 2.

Example 20

Activity of Compound 2 in Airway Inflammation

Figure 3:
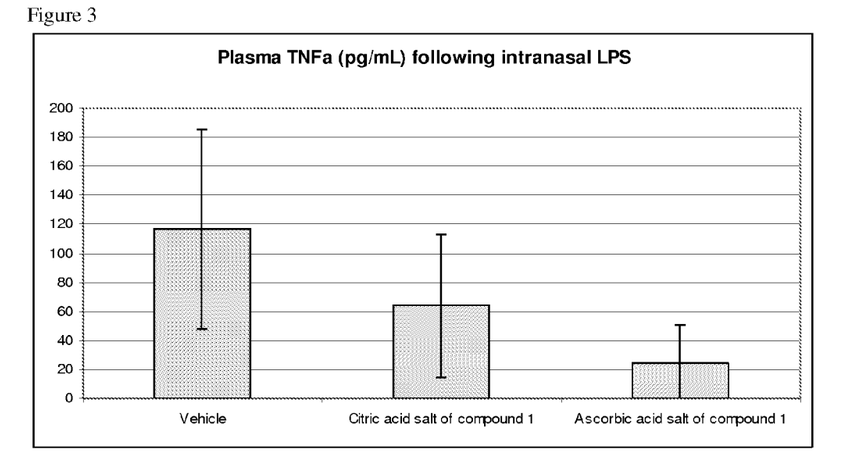
FIG. 3. Effect of compound 1 organic acid salts on release of cytokines from lung into plasma

Airway inflammation is induced by inhalation of solutions containing bacterial LPS. 20 μg per mouse is provided intranasally in phosphate buffered saline. 90 minutes after challenge, plasma is recovered by cardia puncture and frozen prior to analysis for cytokines by ELISA. TNFa is the primary cytokine measured. Compound 1 and acid mixtures are dissolved in water, and the pH of the resulting solution is not greater than 7.0. Compounds are administered 30 minutes prior to challenge either as 1 μL/g of a 100 mM solution intranasal in 22 g BALBc female mice. The results of said interventions include reduction of lung and/or plasma cytokines. Example data are recorded in FIG. 3.

Example 21

Activity in Prevention of Signs of Onset of Muscular Degeneration in MDX Mice

Dystrophin mutant mice (MDX, C57BL/10ScSn-Dmd-mdx/J, Jackson labs) generated by the cross of homozygous females with hemizygous males are provided with either chow, or chow containing 10 mg of Compound 1 per 150 g chow from birth Animals are allowed to consume chow ad libitum. Every 2 weeks from weaning, animals are monitored for open field mobility, grip strength and voluntary activity on a running wheel. At 6 months of age, monitoring is thereafter on a monthly basis Animals in satellite groups are sacrificed at 3, 6 and 9 months and muscle necrosis and cell infiltration is quantified by histology of the soleus, biceps femoris and extensor digitorum longus (EDL) muscles. Muscle mass, infiltration (CD11 and CD45+ cells) and fibre number is compared with age matched control C57BL/10 ScSn mice.

Example 22

Stimulation of Chloride Release in Cystic Fibrosis Cells

CF human primary airway epithelial cells (CF hAEC) on non-CF (S9) were cultured in the presence of compound 1 or azithromycin 10 μM. Cl efflux was monitored by fluorescence of [6-methoxy-N-(3-sulfopronyl)-quinolinium (SPQ). Both compound 1 and azithromycin stimulate Cl efflux as determined by fluorescene change. These data suggest that application of compound 1 or azithromycine modifies permeability of cells towards ions.

What is claimed is:

1. A compound represented by the formula:

wherein
$R_1$=P(=O)(OH)$_2$, S(=O)$_2$(OH), a saccharide or C(=O)-R$_3$, wherein R$_3$=(CH$_2$)$_2$—C(=O)OH or an amino acid;
or a pharmaceutically acceptable salt or formaldehyde adduct thereof.

2. A salt of a compound of claim 1 containing an organic acid anion.

3. A salt of a compound of claim 1 containing acetic, formic, propionic, suberic, malic, citric, maleic, fumaric, succinic, azelaic, pyruvic, alpha ketoglutaric, aspartic, glutamic, sulfonic or ascorbic acids.

4. The compound of claim 1 or pharmaceutically acceptable salt thereof, wherein the compound is:

Compound 9

; or

Compound 10

* * * * *